United States Patent
Bang-Andersen et al.

(10) Patent No.: US 7,772,240 B2
(45) Date of Patent: Aug. 10, 2010

(54) TRANS-1(6-CHLORO-3-PHENYLINDAN-1-YL)-3,3-DIMETHYLPIPERAZINE

(75) Inventors: Benny Bang-Andersen, Copenhagen (DK); Klaus Peter Bogeso, Horsholm (DK); Henrik Svane, Virum (DK); Lars Ole Lyngso, Vekso Sj. (DK); Allan Carsten Dahl, Nyrup (DK); Mark Howells, Havdrup (DK); Klaus Gjervig Jensen, Copenhagen (DK); Tomas Mow, Tureby (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 320 days.

(21) Appl. No.: 10/568,292

(22) PCT Filed: Aug. 18, 2004

(86) PCT No.: PCT/DK2004/000546

§ 371 (c)(1),
(2), (4) Date: Aug. 14, 2006

(87) PCT Pub. No.: WO2005/016901

PCT Pub. Date: Feb. 24, 2005

(65) Prior Publication Data

US 2006/0281758 A1 Dec. 14, 2006

Related U.S. Application Data

(60) Provisional application No. 60/496,058, filed on Aug. 18, 2003, provisional application No. 60/520,246, filed on Nov. 14, 2003.

(30) Foreign Application Priority Data

Aug. 18, 2003 (DK) ................. 2003 01180
Sep. 11, 2003 (DK) ................. 2003 01305

(51) Int. Cl.
*A61K 31/495* (2006.01)
*C07D 241/04* (2006.01)

(52) U.S. Cl. ................. 514/255.03; 544/403
(58) Field of Classification Search ............. None
See application file for complete search history.

(56) References Cited

U.S. PATENT DOCUMENTS

| | | |
|---|---|---|
| 6,410,794 B1 | 6/2002 | Zinnen et al. |
| 6,444,854 B1 | 9/2002 | Dapremont et al. |
| 6,455,736 B1 | 9/2002 | Zinnen et al. |
| 6,506,940 B1 | 1/2003 | Jadav et al. |
| 7,648,991 B2 * | 1/2010 | Bang-Andersen et al. ............. 514/255.03 |

FOREIGN PATENT DOCUMENTS

| | | |
|---|---|---|
| EP | 0 638 073 B1 | 6/2000 |
| WO | WO 93/08799 | 5/1993 |
| WO | WO 95/15299 | 6/1995 |
| WO | WO 2005/016900 | 2/2005 |

OTHER PUBLICATIONS

Robichaud et al. in Annual Reports in Medicinal Chemistry, vol. 36, pp. 11-20 (2000).*
Zhang et al. Expert Opin.Ther.Patents, vol. 16,p. 587-630 (2006).*
Gonzalez-Gomez et al. Bioorganic & Medicinal Chemistry Letters, vol. 13, pp. 175-178 (2003).*
Newman Exp.Opin.Ther.Patents, vol. 10, pp. 1095-1122 (2000).*
Froimowits, et al., J. Med. Chem. 2000, 43, 4981-4992.
Bogeso J. Med. Chem., 1985, 28, 1817-1828.
Balsara, J.J., et al. Effect of Drugs Influencing Central Serotonergic Mechanisms on Haloperidol-Induced Catalepsy. Psychopharmacol. 1972. 62:67-69.
Bertz, R.J., et al. Use of In Vitro and In Vivo Data to Estimate the Likelihood of Metabolic Pharmacokinetic Interactions. Clin. Pharmacokinet. 1997. 32(3):210-258.
Carlsson, A. Antipsychotic Drugs, Neurotransmitters, and Schizophrenia. Am. J. Psych. 1978. 135(2):164-173.
Carlsson, L., et al. QTU-Prolongation and Torsades de Pointes Induced by Putative Class III Antiarrhythmic Agents in the Rabbit: Etiology and Interventions. J. Cardiovasc. Pharmacol. 1990. 16:276-285.
Chauret, N., et al. The Use of 3-[2-(N,N-Diethyl-N-Methylammonium)Ethyl]-7-Methoxy-4-Methylcoumarin (AMMC) as a Specific CYP2D6 Probe in Human Liver Microsomes. Drug Metab. Dispos. 2001. 29(9):1196-1200.
Clark, W.M., et al. A Highly Enantioselective Conjugate Reduction of 3-Arylinden-1-ones Using Bakers' Yeast for the Preparation of (S)-3-Arylindan-1-ones. Org. Lett. 1999. 1(11):1839-1842.
Clark, W.M., et al. A Catalytic Enantioselective Synthesis of the Endothelin Receptor Antagonists SB-209670 and SB-217242: A Base-Catalyzed Stereospecific Formal 1,3-Hydrogen Transfer of a Chiral 3-Arylindenol. J. Am. Chem. Soc. 1998. 120:4550-4551.
Cossy, J., et al. Synthesis of Indatraline Using a Suzuki Cross-Coupling Reaction and a Chemoselective Hydrogenation: A Versatile Approach. Synlett. 2003. 10:1515-1517.
Darpö, B. Spectrum of Drugs Prolonging QT Interval and the Incidence of Torsades de Pointes. Eur. Heart J. Suppl. 2001. 3 Suppl. K:K70-K80.
Ereshefsky, L., et al. Serotonin Selective Reuptake Inhibitor Drug Interactions and the Cytochrome P450 System. J. Clin. Psych. 1996. 57(Suppl. 8):17-25.
Glassman, A. H. et al. Antipsychotic Drugs: Prolonged QTc Interval, Torsade de Pointes, and Sudden Death. Am J Psychiatry. 2001. 158(11):1774-1782.

(Continued)

*Primary Examiner*—Emily Bernhardt
(74) *Attorney, Agent, or Firm*—Stephen G. Kalinchak; Margaret M. Buck

(57) ABSTRACT

A compound 4-((1R,3S)-6-Chloro-3-phenylindan-1-yl)-2,2-dimethylpiperazine and salts thereof, pharmaceutical compositions comprising the compound and salts, and medical use thereof, including for treatment of schizophrenia and other psychotic disorders.

10 Claims, No Drawings-

OTHER PUBLICATIONS

Gu, X. H. et al. Design, Synthesis, and Monoamine Transporter Binding Site Affinities of Methoxy Derivatives of Indatraline. J. Med. Chem. 2000. 43:4868-4876.

Hyttel, J. et al. Neurochemical Profile of Lu 19-005, a Potent Inhibitor of Uptake of Dopamine, Noradrenaline, and Serotonin. J. Neurochem. 1985. 44:1615-1622.

Lin, J. H. et al. Role of Pharmacokinetics and Metabolism in Drug Discovery and Development. Pharmacological Reviews. 1997. 49(4):403-449.

Raehl, C. L. et al. Drug-induced torsade de pointes. Clin. Pharm. 1985. 4:675-690.

Rendic, S. et al. Human Cytochrome P450 Enzymes: A Status Reort Summarizing Their Reactions, Substrates, Inducers, and Inhibitors. Drug Metab. Rev. 1997. 29(1&2):413-580.

Schulman, R.W. et al. Psychotropic Medications and Cytochrome P450 2D6: Pharmacokinetic Considerations in the Elderly. Can. J. Psych. 1997. 42(suppl 1):4S-9S.

Woosley, R. L. Cardiac Actions of Antihistamines. Ann. Rev. Pharmacol. Toxicol. 1996. 36:233-252.

Yap, Y.G. et al. The current cardiac safety situation with antihistamines. Clin. Exper. Allergy. 1999. 29(suppl 1):15-24.

Yun, J. et al. Efficient Kinetic Resolution in the Asymmetric Hydrosilylation of Imines of 3-Substituted Indanones and 4-Substituted Tetralones. J. Org. Chem. 2000. 65:767-774.

Haleblian, John, et al., "Pharmaceutical Applications of Polymorphism", Journal of Pharmaceutical Sciences, Aug. 1969, pp. 911-929, vol. 58, No. 8.

Davies, Huw M. L., et al., "Asymmetric Synthesis of (+)-Indatraline Using Rhodium-Catalyzed C-H Activation", Tetrahedron Letters, 2002, pp. 4951-4953, 43, Pergamon.

Willner, P. Dopamine and Depression: A Review of Recent Evidence. II. Theoretical Approaches. Brain Res. Rev. 1983. 6(3):225-236.

Willner, P. Dopamine and Depression: A Review of Recent Evidence. III. The Effects of Antidepressant Treatments. Brain Res. Rev. 1983. 6(3):237-246.

Klaus P. Bogeso, et al., "Enhanced D1 Affinity in a Series of Piperazine Ring Substituted 1-Piperazino-3-Arylindanes with Potential Atypical Antipsychotic Activity", Journal of Medicinal Chemistry, vol. 38, No. 22, 1995, pp. 4380-4392.

Bogeso, Klaus P. et al. "Stereospecific and Selective 5-HT2 Antagonism in a Series of 5-Substituted trans-1-Piperazino-3-phenylindans". J. Med.Chem. 1993. 36:2761-2770.

* cited by examiner

TRANS-1(6-CHLORO-3-PHENYLINDAN-1-YL)-3,3-DIMETHYLPIPERAZINE

This application is a §371 national stage of PCT International Application No. PCT/DK2004/000546, filed Aug. 18, 2004 on behalf of H. Lundbeck A/S, which is a continuation-in-part of and claims priority of Danish Application No. PA 200301180, filed Aug. 18, 2003 and Danish Application No. PA 200301305, filed Sep. 11, 2003, and claims benefit of U.S. Provisional Application No. 60/496,058 filed Aug. 18, 2003 and U.S. Provisional Application No. 60/520,246 filed Nov. 14, 2003, the contents of all of which are hereby incorporated by reference into the subject application.

The present invention relates to trans-1-(6-chloro-3-phenylindan-1-yl)-3,3-dimethylpiperazine and salts thereof, in particular for medical use, including for treatment of schizophrenia or other diseases involving psychotic symptoms.

BACKGROUND OF THE INVENTION

The compound, which is the subject of the present invention (Compound I, trans-1-((1R,3S)-6-chloro-3-phenylindan-1-yl)-3,3-dimethylpiperazine) has the general formula (1).

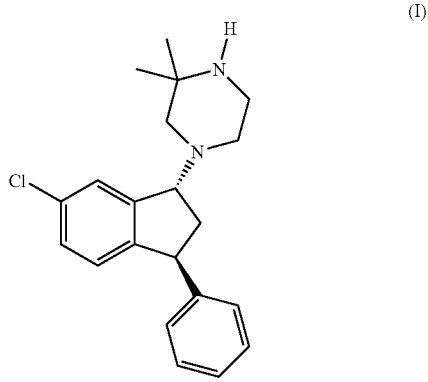

A group of compounds structurally related to Compound I, i.e. trans isomers of 3-aryl-1-(1-piperazinyl)indanes substituted in the 2- and/or 3-position of the piperazine ring, has been described in EP 638 073; Bøgesø et al. in J. Med. Chem., 1995, 38, 4380-4392 and Klaus P. Bøgesø in "Drug Hunting, the Medicinal Chemistry of 1-Piperazino-3-phenylindans and Related Compounds", 1998, *ISBN 87-88085-10-4I*. These compounds are described as having high affinity for dopamine (DA) $D_1$ and $D_2$ receptors and the 5-$HT_2$ receptor and are suggested to be useful for treatment of several diseases in the central nervous system, including schizophrenia.

An enantiomer corresponding to the compound of the formula (I) but differing in that it has a methyl group instead of a hydrogen on the piperazine has been disclosed in Bøgesø et al. in J. Med. Chem., 1995, 38, 4380-4392, see table 5, compound (−)-38. This publication concludes that the (−)-enantiomers of compound 38 is a potent $D_1/D_2$ antagonists showing some $D_1$ selectivity in vitro while in vivo it is equipotent as $D_1$ and $D_2$ antagonist. The compound is described as a potent 5-H $T_2$ antagonist, having high affinity for $\alpha_1$ adrenoceptors.

None of the above references disclose the specific enantiomeric form above (Compound I) or the medical use thereof. The trans isomer in the form of the racemate of Compound 1 is only indirectly disclosed as an intermediate in the synthesis of compound 38 in Bøgesø et al. in J. Med. Chem., 1995, 38, 4380-4392) while the medical use of Compound I or of its corresponding racemate is not described.

The aetiology of schizophrenia is not known, but the dopamine hypothesis of schizophrenia (Carlsson, Am. J. *Psychiatry* 1978, 135, 164-173), formulated in the early 1960s, has provided a theoretical framework for understanding the biological mechanisms underlying this disorder. In its simplest form, the dopamine hypothesis states that schizophrenia is associated with a hyperdopaminergic state, a notion which is supported by the fact that all antipsychotic drugs on the market today exert some dopamine $D_2$ receptor antagonism (Seeman *Science and Medicine* 1995, 2, 28-37). However, whereas it is generally accepted that antagonism of dopamine $D_2$ receptors in the limbic regions of the brain plays a key role in the treatment of positive symptoms of schizophrenia, the blockade of $D_2$ receptors in striatal regions of the brain causes extrapyramidal symptoms (EPS). As described in EP 638 073 a profile of mixed dopamine $D_1/D_2$ receptor inhibition has been observed with some so-called "atypical" antipsychotic compounds, in particular with clozapine, used in treatment of schizophrenic patients. Central al antagonistic actions has also been suggested to contribute in improving antipsychotic properties (Millan et al, *JPET,* 2000, 292, 38-53).

Further, selective $D_1$ antagonists have been connected to treatment of sleep disorders and alcohol abuse (D. N. Eder, *Current Opinion in Investigational Drugs,* 2002 3(2):284-288). Dopamine may also play an important role in the etiology of affective disorders (P. Willner, *Brain. Res. Rev.* 1983, 6, 211-224, 225-236 and 237-246; *J. Med. Chem.* 1985, 28, 1817-1828).

In EP 638 073 is described how compounds having affinity for 5-$HT_2$ receptors, in particular 5-$HT_2$ receptors antagonists, have been suggested for treatment of different diseases, such as schizophrenia including the negative symptoms in schizophrenic patients, depression, anxiety, sleep disturbance, migraine attacks and neuroleptic-induced parkinsonism. 5-$HT_2$ receptor antagonism has also been suggested to reduce the incidence of extrapyramidal side effects induced by classical neuroleptics (Balsara et al. *Psychopharmacology* 1979, 62, 67-69).

DETAILED DESCRIPTION OF THE INVENTION

The Products of the Invention and the Medical use Thereof

The inventors have found that Compound I displays high affinity for dopamine D1 receptors, dopamine D2 receptors and for alfa1 adrenoceptors. Furthermore, compound I has been found to be an antagonist at dopamine D1 and D2 receptors, and at serotonin 5-HT2a receptors. The pharmacological activities of compound I are with respect to these receptors found to be similar to that of the compound described above differing structurally from Compound I in that it has a methyl group instead of a hydrogen on the piperazine.

The inventors have also found that several of the structurally related compounds, both racemates and enantiomers, described in the above mentioned references are CYP2D6 (Cytochrome P450 2D6) inhibitors whereas Compound I is a relatively weak inhibitor of CYP2D6, also in comparison with other antipsychotics such as Haloperidole and Risperidone. The racemate of the compound of the present invention is also considerable more potent on the CYP2D6 enzyme compared to the enantiomer of the present invention, i.e. Compound I.

The CYP2D6 enzyme is a liver enzyme important for metabolism. CYP2D6 is a mammalian enzyme commonly associated with the metabolism of pharmaceutical compounds and inhibition of this drug metabolizing enzyme may lead to clinically significant drug-drug interactions i.e. if two drugs are given in combination and are metabolised by the same enzymes, competition for metabolism may give rise to increased plasma concentrations and therefore possible adverse effects (for review see Lin et al, *Pharmacological Rev.* 1997, 49, 403-449, Bertz R J and Granneman G R. *Clin Pharmacokinet* 1997, 32,210-258).

Since more than 80 drugs in clinical use (and in particular psychotropic drugs) are metabolized by CYP2D6 (Bertz R J, Granneman G R. *Clin Pharmacokin* 1997, 32, 210-58, Rendic S, DiCarlo F J. *Drug Metab Rev* 1997, 29, 413-580), inhibition of this enzyme by coadministered drugs can lead to dramatic increases in exposure levels and resulting toxicity as seen with the combination of the well known CYP2D6 inhibitors fluoxetine or paroxetine in combination with Imipramine, Desimipramine or Nortriptyline, resulting in increased cadiac toxicity of these tricyclics (Ereshefsky L. el al. *J. Clin. Psychiatry* 1996, 57(supp18), 17-25, Shulman R W *Can J Psychiatry, Vol* 42, Supplement 1, 4S).

The fact that Compound I has a low interaction with the liver enzyme CYP2D6 means that it has a reduced potential for drug to drug interaction, i.e. there is possibly less drug to drug interaction when a patient is treated with the compound of the present invention together with other drugs which are mainly metabolised by the CYP2D6 enzyme. This is a considerable advantage, in particular for patients with schizophrenia which are often treated with other medicaments to control their disease.

The inventors have also found that Compound I has a relatively low prolonging effect on the QT-interval in the electrocardiogram (ECG) of the "alpha-chloraose anaesthetised rabbit". Drug-induced QT-interval prolongation in the electrocardiogram (ECG) and the appearance of fatal cardiac arrhythmias, torsade de pointes (TdP), has become recognised as a potential risk during treatment with a broad range of drugs including repolarisation-delaying antiarrhythmics [C. L. Raehl, A. K. Patel and M. LeRoy, *Clin Pharm* 4 (1985), 675-690], various antihistamines [R. L. Woosley, *Annu Rev Pharmacol Toxicol* 36 (1996), 233-252; Y. G. Yap and A. J. Camm, *Clin Exp Allergy* 29 Suppl 1 (1999), 15-24], antipsychotics [A. H. Glassman and J. T. Bigger, *Am J Psychiatry* 158 (2001), 1774-1782] and anti-microbial agents [B. Darpö, Eur *Heart J* 3 Suppl K (2001), K70-K80]. The fact that Compound I has a relatively low effect on the rabbit QT interval means that this compound has a reduced potential for introducing drug-induced QT interval prolongation and appearance of fatal cardiac arrhythmias, torsade de pointes (TdP), in humans compared to several commercialised antipsychotics.

Thus, in one aspect, the invention relates to the compound of formula I (Compound I) and salts thereof. The salt of the invention, i.e. of the compound of formula (I), may, e.g., be selected from a fumarate or a maleate salt of Compound I.

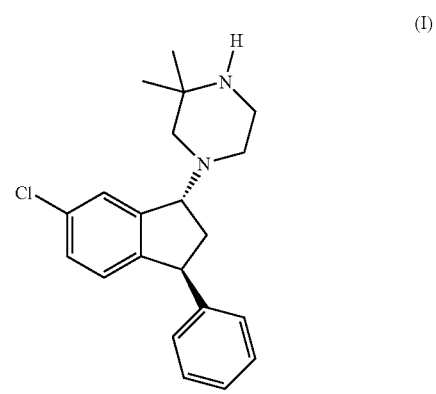

The properties of Compound I indicate that it will be particularly useful as a pharmaceutical. Accordingly, the present invention further relates to a pharmaceutical composition of Compound I of the invention or a salt thereof. The invention also relates to the medical use of such compounds, salts and compositions, such as for the treatment of a disease in the central nervous system, including psychosis, in particular schizophrenia or other diseases involving psychotic symptoms, such as, e.g., Schizophrenia, Schizophreniform Disorder, Schizoaffective Disorder, Delusional Disorder, Brief Psychotic Disorder, Shared Psychotic Disorder as well other psychotic disorders or diseases that present with psychotic symptoms, e.g. mania in bipolar disorder.

Additionally, the 5-$HT_2$ antagonistic activity of the compound of the invention suggests that the compound or salt thereof may have a relatively low risk of extrapyramidal side effects.

The present invention also relates to use of Compound I of the invention, or a salt thereof for treatment of a disease selected from the group consisting of anxiety disorders, affective disorders including depression, sleep disturbances, migraine, neuroleptic-induced parkinsonism, cocaine abuse, nicotine abuse, alcohol abuse and other abuse disorders.

In a preferred embodiment, the present invention relates to a method of treating Schizophreniform Disorder, Schizoaffective Disorder, Delusional Disorder, Brief Psychotic Disorder, Shared Psychotic Disorder or mania in bipolar disorder, comprising administering a therapeutically effective amount of Compound I of the invention or a salt thereof.

A further embodiment of the invention relates to a method of treating positive symptoms of 5 schizophrenia comprising administering a therapeutically effective amount of Compound I or a salt thereof.

Another embodiment of the invention relates to a method of treating negative symptoms of schizophrenia comprising administering a therapeutically effective amount of the Compound I or a salt thereof.

A further embodiment of the invention relates to a method of treating depressive symptoms of schizophrenia comprising administering a therapeutically effective amount of Compound I or a salt thereof.

A further aspect of the invention relates to a method of treating mania and/or maintenance of bipolar disorder comprising administering a therapeutically effective amount of Compound I or a salt thereof.

A further aspect of the invention relates to a method of treating neuroleptic-induced parkinsonism comprising administering a therapeutically effective amount of the Compound I or a salt thereof.

The invention further relates to a method of treating substance abuse, e.g. nicotine, alcohol or cocaine abuse, comprising administering a therapeutically effective amount of Compound I or a salt thereof.

In a broad aspect, the present invention relates to trans-1-(6-chloro-3-phenylindan-1-yl)-3,3-dimethylpiperazine or a salt thereof for use as a medicament.

Accordingly, the present invention also relates to a method of treating a disease selected from the group consisting of a disease involving psychotic symptoms, schizophrenia (e.g. one or more of positives symptoms, negative symptoms and depressive symptoms of schizophrenia), Schizophreniform Disorder, Schizoaffective Disorder, Delusional Disorder, Brief Psychotic Disorder, Shared Psychotic Disorder, and mania in bipolar disorder, anxiety disorders, affective disorders including depression, sleep disturbances, migraine, neuroleptic-induced parkinsonism, and abuse disorders, e.g. cocaine abuse, nicotine abuse, or alcohol abuse, comprising administering a therapeutically effective amount of the compound trans-1-(6-chloro-3-phenylindan-1-yl)-3,3-dimethylpiperazine or a salt thereof.

As used herein the term "trans-1-(6-chloro-3-phenylindan-1-yl)-3,3-dimethylpiperazine", i.e. without any specific indication of the enantiomer form (e.g. using (+) and (−), or using the R/S-convention, is meant to refer to any enantiomeric form of this compound, i.e. either of the two enantiomers or to a mixture of the two, e.g. the racemic mixture). However, in this context preferably the content of the enantiomer corresponding to that of Compound I is at least 50%, i.e. at least as the racemic mixture, but preferably Compound I is in enantiomeric excess.

In the present context for the pharmaceutical uses it is understood that when specifying the enantiomer form as done in formula (I) for Compound I, then the compound is relatively stereochemically pure, preferably the enantiomeric excess is of at least 70%, and more preferably at least 80% (80% enantiomeric excess means that the ratio of I to its enantiomer is 90:10 in the mixture in question) at least 90%, at least 96%, or preferably at least 98%. In a preferred embodiment, the diastereomeric excess of Compound I is at least 90% (90% diastereomeric purity means the ratio of Compound I to cis-1-((1S,3S)-6-chloro-3-phenylindan-1-yl)-3,3-dimethylpiperazine is 95:5), at least 95%, at least 97%, or at least 98%.

A further aspect of the invention relates to a method of treatment as described herein, wherein the patient treated with Compound I or a salt thereof is also treated with at least one other medicament. A particular relevant embodiment in this connection, is treatment with other medicaments being metabolised by CYP2D6.

In a suitable embodiment, the other medicament is an antipsychotic. Accordingly, one embodiment relates to the use of a compound, salt or pharmaceutical composition of the invention for treating a patient suffering from schizophrenia or other psychoses who is also treated with other medicament(s), e.g. where this other medicament is an antipsychotic.

In another embodiment, the invention relates to the use of a compound or a salt of the invention for treating a patient suffering from schizophrenia or other psychoses who is a substance abuser, e.g. of alcohol or narcotics.

The compound, salt or composition of the invention may be administered in any suitable way e.g. orally, buccal, sublingual or parenterally, and the compound or salt may be presented in any suitable form for such administration, e.g. in the form of tablets, capsules, powders, syrups or solutions or dispersions for injection. In one embodiment, the compound or salt of the invention are administered in the form of a solid pharmaceutical entity, suitably as a tablet or a capsule.

Methods for the preparation of solid pharmaceutical preparations are well known in the art. Tablets may thus be prepared by mixing the active ingredient with ordinary adjuvants, fillers and diluents and subsequently compressing the mixture in a convenient tabletting machine. Examples of adjuvants, fillers and diluents comprise corn starch, lactose, talcum, magnesium stearate, gelatine, lactose, gums, and the like. Any other adjuvant or additive such as colourings, aroma, preservatives, etc. may also be used provided that they are compatible with the active ingredients.

Solutions for injections may be prepared by dissolving a salt of the invention and possible additives in a part of the solvent for injection, preferably sterile water, adjusting the solution to desired volume, sterilisation of the solution and filling in suitable ampules or vials. Any suitable additive conventionally used in the art may be added, such as tonicity agents, preservatives, antioxidants, solubilising agents etc.

The daily dose of the compound of formula (I) above, calculated as the free base, is suitably between 1.0 and 160 mg/day, more suitable between 1 and 100 mg, e.g. preferably between 2 and 55 mg.

The term "treatment" as used herein in connection with a disease or disorders includes also prevention as the case may be.

Method of Preparation

The compound of formula (I) in racemic form may, e.g., be prepared analogously to the methods outlined in EP 638 073, and in Bøgesø et al. J. Med. Chem., 1995, 38, page 4380-4392 followed by optical resolution of the racemic compound by crystallisation of diastereomeric salts thereby obtaining the enantiomer of formula (I).

The present inventors have developed a route of synthesis in which the enantiomer of formula (I) is obtained via a synthetic sequence starting from enantiomeric pure V, i.e. compound Va ((1S,3S)-6-chloro-3-phenylindan-1-ol, see below). Thus, in this process, the intermediate of formula V is resolved, e.g. by chiral chromatography or enzymatically, to obtain the enantiomer of formula Va. This new route of synthesis to obtain the compound of formula (I) is more efficient than the above mentioned crystallisation of diastereomeric salts of the final product I, e.g. the resolution of an intermediate instead of the final product gives a much more efficient synthesis, as only the wanted enantiomer is used in the subsequent steps, giving e.g. higher volume yields and less consumption of reagents.

Accordingly, the enantiomer of formula (I) may be obtained by a process involving the following steps:

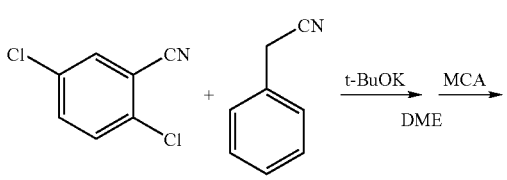

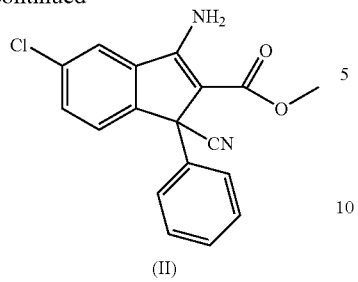

(II)

Benzyl cyanide is reacted with 2,5-dichlorobenzonitril in the presence of a base, suitably potassium tert-butoxide (t-BuOK) in a suitable solvent such as dimethyl ether (DME), further reaction with methyl chloro acetate (MCA) leads to spontaneous ring closure and one pot formation of the compound of formula (I).

The compound of formula (II) is then subjected to acidic hydrolysis to form a compound of formula (III), suitably by heating in a mixture of acetic acid, sulphuric acid and water, and thereafter decarboxylation by heating the compound of formula (III) in a suitable solvent, such as toluene with triethyl amine or N-methyl pyrrolidin-2-one (NMP), to form a compound of formula (IV).

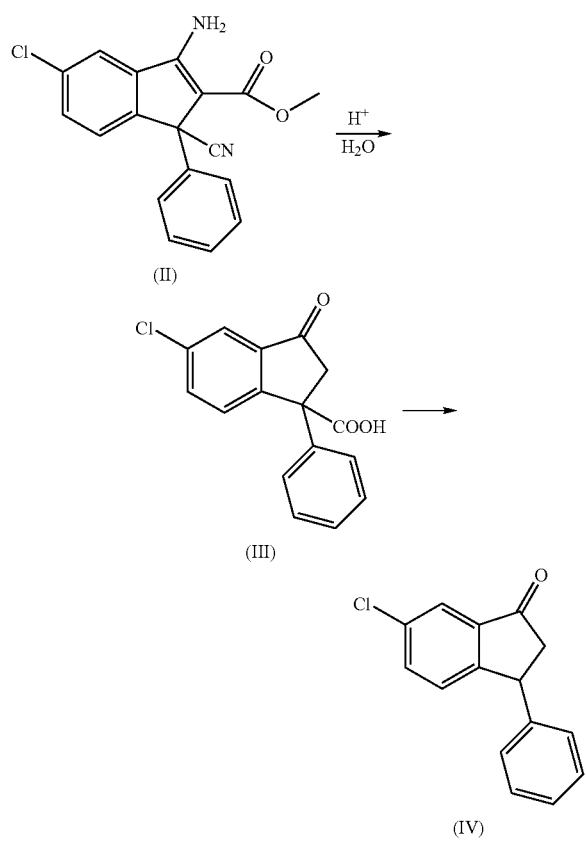

The compound of formula (IV) is then reduced, suitably with sodium borohydride (NaBH$_4$) in a solvent such as an alcohol, e.g. ethanol or iso-propanol, and preferably at a temperature in the range of −30° to +30° C., e.g. below 30° C., below 20° C., below 10° C., or preferably below 5° C., to form a compound of formula (V) with cis configuration:

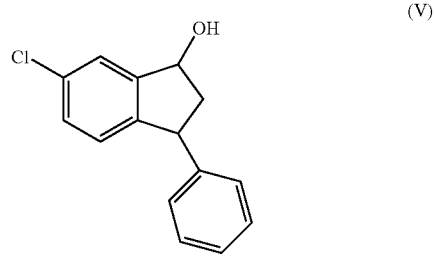

The compound of formula (V) is resolved to achieve the desired enantiomer (formula Va), i.e. also with cis configuration ((1S,3S)-6-chloro-3-phenylindan-1-ol):

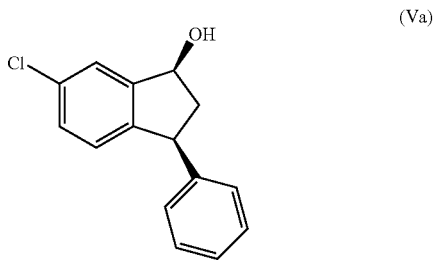

The resolution of (V) to (Va) may, e.g., be performed using chiral chromatography, preferably liquid chromatography, suitably on a chiral column of silicagel coated with a chiral polymer, e.g. a modified amylose, preferably amylose tris-(3, 5-dimethylphenylcarbamate) coated on silicagel. A suitable solvent is used for the chiral liquid chromatography, such as, e.g. an alcohol, a nitrile, an ether, or an alkane, or mixtures thereof, suitably ethanol, methanol, iso-propanol, acetonitrile, or methyl tert-butyl ether or mixtures thereof, preferably methanol or acetonitrile. The chiral liquid chromatography can be scaled up using suitable technologies, e.g. simulated moving bed technology (SMB).

Alternatively, the compound of formula (V) is resolved to achieve Compound Va by enzymatic resolution. It has been found that enantiomerically pure Compound Va, or acylated derivatives thereof, may be prepared by enzymatic enantioselective acylation of the hydroxyl group in racemic Compound V to obtain Compound Va or an acylated derivative thereof with high optical purity. Alternatively, enantiomerically pure Compound Va may also be obtained by a process comprising converting racemic Compound V to the corresponding ester derivative,. i.e. an ester group at the hydroxyl position followed by an enzymatic enantioselective deacylation. Use of enzymatic enantioselective deacylation has been reported for other compounds.

Accordingly, the resolution of Compound V to Compound Va may be performed by selective enzymatic acylation. Selective enzymatic acylation means that the enzymatic acylation is preferentially effective for conversion of one of the cis-enantiomers of the compound of formula V to the corresponding acetylated derivative Vb leaving the other cis-enantiomer of Compound V, e.g. compound Va, as unconverted in the reaction mixture as outlined in the following:

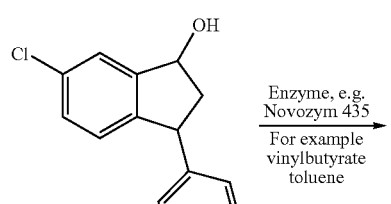

V

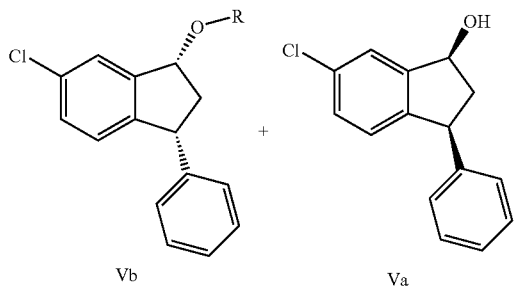

Vb      Va wherein R, e.g., is acetate, propionate, butyrate, valerate, hexanoate, benzoate, laurate, isobutyrate, 2-methylbutyrate, 3-methylbutyrate, pivalate, 2-methylvalerate, 3-methylvalerate, or 4-methylvalerate. Suitable irreversible acyldonors are, e.g, vinyl-esters, 2-propenyl-esters or 2,2,2-trihalid-ethyl-esters. Alternatively, the other enantiomer is acetylated (i.e. acetylated Va is the product, not shown), and the alcohol Va can subsequently be obtained by isolation of acetylated Va and subsequent removal of the ester group.

Alternatively, The resolution of Compound V to Compound Va may be performed by selective enzymatic deacylation. Selective enzymatic deacylation means that the enzymatic deacylation is preferentially effective for conversion of one of the esters of compound of formula V (Vc), leaving the other cis-enantiomer of esters of a compound of formula V (Vd) as unconverted in the reaction mixture.

Suitable esters (Vc) of the compound of formula (V) are esters such as acetate, propionate, butyrate, valerate, hexanoate, benzoate, laurate, isobutyrate, 2-methylbutyrate, 3-methylbutyrate, pivalate, 2-methylvalerate, 3-methylvalerate, 4-methylvalerate,

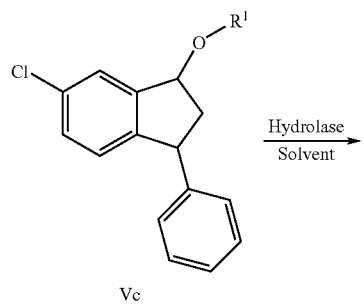

Vc

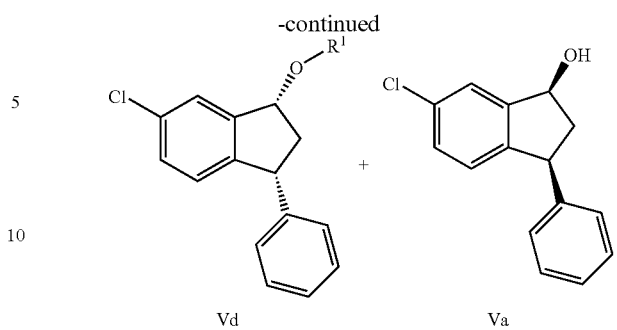

Vd      Va wherein $R^1$, e.g., is acetate, propionate, butyrate, valerate, hexanoate, benzoate, laurate, isobutyrate, 2-methylbutyrate, 3-methylbutyrate, pivalate, 2-methylvalerate, 3-methylvalerate, or 4-methylvalerate. Alternatively the ester of Va is left unconverted in the reaction mixture (i.e. acetylated Va is the product, not shown) and the alcohol Va can subsequently be obtained by isolation of acetylated Va and subsequent removal of the ester group by standard procedures.

Thus, enantioselective enzymatic acylation means that the enzymatic acylation is preferentially effective for conversion of one of the enantiomers of a compound of formula (V) preferentially leaving the other enantiomer of the compound of formula (V) unconverted in the reaction mixture. Enantioselective enzymatic deacylation means that the enzymatic deacylation is preferentially effective for conversion of one of the enantiomers of a compound of formula (Vc), preferentially leaving the other enantiomer of the compound of formula (Vc) unconverted in the reaction mixture.

Thus, one embodiment relates to a process for the preparation of the (S, S)— or (R, R)-enantiomer of the compound of formula V (i.e. with cis configuration) comprising:

a) subjecting a racemic Compound V to enantioselective enzymatic acylation using an acylating agent, or b) subjecting a racemic Compound Vc to entantioselective enzymatic deacylation to form a mixture of deacylated Compound Va.

The mixtures obtained by the enzymatic resolution may not be entirely pure, e.g. they may contain a smaller amount of the other enantiomer in addition to a larger amount of the desired enantiomer (Va). The composition mixture obtained after acylation or deacylation according to the invention depend, e.g., on the specific hydrolase used and the conditions under which the reaction is carried out. Characteristic of the enzymatic acylation/deacylation according to the invention is that a considerably larger portion of one enantiomer is converted than of the other. The enantioselective acylation according to the invention thus results in a mixture containing preferentially the compound of formula (Vb) in the (R,R)-form and the compound of formula (Va) in the (S,S)-form, or it may result in a mixture containing preferentially the compound of formula (Vb) in the (S,S)-form and the compound of formula (Va) in the (R,R)-form. Likewise, the enantioselective enzymatic deacylation may result in a mixture containing preferentially the compound of formula (Vd) in the (S,S)-form and the compound of formula (Va) in the (R,R)-form, or it may result in a mixture containing preferentially the compound of formula (Vd) in the (R,R)-form and the compound of formula (Va) in the (S,S)-form. The optical purity of the Va obtained by the optical resolution method of the present invention is usually at least 90% ee., preferably at least 95% ee., more preferably at least 97% ee and most preferably at least 98% ee. However, lower values for the optical purity are acceptable.

According to the invention, enantioselective enzymatic acylation is carried out under conditions substantially suppressing hydrolysis. Hydrolysis, which is the reverse reaction of the acylation reaction, takes place if water is present in the reaction system. Thus, enantioselective enzymatic acylation is preferably carried out in a water-free organic solvent or almost anhydrous organic solvent (enzymes normally require the presence of some water to be active). Suitable solvents include hydrocarbons such as hexane, heptane, benzene and toluene; ethers such as diethyl ether, diisopropyl ether, tetrahydrofuran, 1,4-dioxane, tert-butyl methyl ether and dimethoxyethane; ketones such as acetone, diethyl ketone, butanon, and methyl ethyl ketone; esters such as methyl acetate, ethyl acetate, ethyl butyrate, vinyl butyrate and ethyl benzoate; halogenated hydrocarbons such as methylene chloride, chloroform and 1,1,1-trichloroethane; secondary and tertiary alcohols, such as tert-butanol; nitrogen-containing solvents such as dimethylformamide, acetoamide, formamide, acetonitrile and propionitrile; and aprotic polar solvents such as dimethylsulfoxide, N-methylpyrrolidin-2-one and hexamethylphosphorous triamide. Preferred organic solvents for enzymatic acylation are organic solvents such as toluene, hexane, heptane, dioxane and tetrahydrofuran (THF).

Suitable irreversible acyldonors are, e.g., acyldonors such as vinyl-esters, 2-propenyl-esters or 2,2,2-trihalid-ethyl-esters.

Enantioselective enzymatic deacylation is preferably carried out in water or a mixture of water and an organic solvent, suitable in presence of a buffer. Suitable organic solvents, e.g., are solvents miscible with water such as alcohols, acetonitrile, dimethyl formamide (DMF), dimethyl sulfoxide (DMSO), 1,4-dioxane, DME and diglyme.

It has been found that enzymatic acylation according to the invention may be carried out using Novozym 435 (Candida Antarctica lipase B, from Novozymes A/S, Fluka Cat.-No. 73940). In general, the enzymatic acylation or deacylation according to the invention is preferably carried out using a lipase, an esterase, an acylase or a protease. The enzymes useful according to the invention are such enzymes capable of performing R-selective acylation or S-selective acylation of the hydroxy group in the racemic compound of formula (V) or such enzymes which are capable of performing R-selective deacylation or S-selective deacylation of the acyl group in the racemic compound of formula (Vc). In particular immobilized forms of the enzyme, including Cross-Linked Enzyme Crystal (CLEC) are useful according to the invention. A preferred embodiment relates to use of a lipase for carrying out the enzymatic resolution of Compound V. The most preferred lipase is Candida antarctica lipase (Fluka Cat.-No. 62299); Pseudomonas cepacia lipase (Fluka Cat.-No. 62309); Novozym CALB L (Candida antarctica lipase B) (Novozymes A/S); Novozym 435 (Candida antarctica lipase B) (Novozymes A/S); or Lipozyme TL IM (Thermomyces lanuginosus lipase) (Novozymes A/S), preferably in immobilized form.

The alcohol group of the cis-alcohol of formula (Va) is converted to a suitable leaving group, such as, e.g., a halogen, e.g. Cl or Br, preferably Cl, or a sulphonate, e.g. mesylate or tosylate, suitably by reaction with an agent, such as thionyl chloride, mesyl chloride or tosyl chloride, in an inert solvent, e.g. an ether, suitably tetrahydrofuran. The resulting compound has formula (VI), where LG is the leaving group:

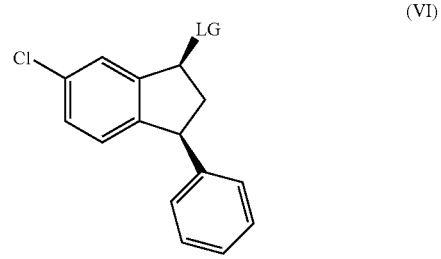

In a preferred embodiment, LO is Cl, i.e. the cis-chloride of formula (VIa):

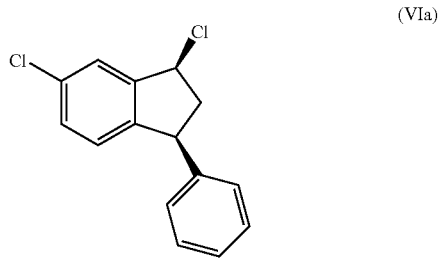

Compound VI, e.g. with LG as chloro, is then reacted with 2,2-dimethylpiperazine in a suitable solvent, e.g. a ketone such as, e.g., methyl isobutyl ketone or methyl ethyl ketone, preferably methyl isobutyl ketone in presence of a base, such as e.g., potassium carbonate, to obtain Compound I.

Furthermore, the piperazine part of the molecule may be introduced by reacting Compound VI with a compound of formula (VII) below, where PG is a protecting group such as, but not restricted to, e.g. phenylmethoxycarbonyl (often called Cbz or Z), tert-butyloxycarbonyl (often called BOC), ethoxycarbonyl, or benzyl, thereby obtaining the compound of formula (VIII) below. Compound VIII is subsequently deprotected to Compound I.

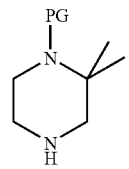

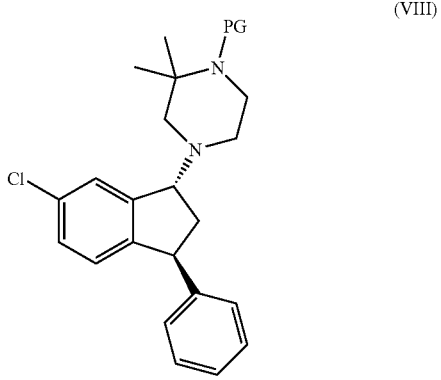

During the synthesis some cis diastereoisomer of Compound I (i.e. 1-((1S,3S)-6-chloro-3-phenylindan-1-yl)-3,3-dimethylpiperazine) is formed as an impurity in the final product. This impurity is due mainly to the formation of some of the trans form of (VI) (e.g. (1S,3R)-3,5-dichloro-1-phenylindan when LG is Cl) in the step where Compound VI is formed. Therefore, the impurity can be minimized by crystallisation of the desired cis form of Compound VI, from the mixture of trans and cis (VI); in the case where LG is Cl in Compound VI this can be done by stirring the mixture with a suitable solvent, e.g. an alkane, such as heptane, whereby the desired cis form of VI precipitates and the undesired trans form of Compound VI goes into solution. The desired cis form of Compound VI (e.g. when LG is Cl) is isolated by filtration, washed with the solvent in question and dried.

The cis form of Compound I may also be removed by precipitation of a suitable salt of the compound of formula Compound I, e.g. a salt of an organic acid, such as an organic diacid, suitably a fumarate salt or a maleate salt of the compound of formula (I), optionally followed by one more re-crystallisations.

The invention in further aspects also relates to the intermediates as described herein for the synthesis of the compound of formula (I), i.e. in particular the intermediates Va and VI, including Compound VIa. In this context is understood that when specifying the stereoisomeric form, then the stereoisomer is the main constituent of the compound. In particular, when specifying the enantiomeric form, then the compound has an enantiomeric excess of the enantiomer in question.

Accordingly, one embodiment of the invention relates to the compound of formula (Va), preferably having an enantiomeric excess of at least 60% (60% enantiomeric excess means that the ratio of Va to its enantiomer is 80:20 in the mixture in question), at least 70%, at least 80%, at least 85%, at least 90%, at least 96%, preferably at least 98%. Furthermore, the diastereomeric excess of the compound is preferably at least 70% (70% diastereomeric excess means, that the ratio of Compound Va to (1R,3S)-6-chloro-3-phenylindan-1-ol is 85:15 in the mixture in question), at least 80%, at least 85%, at least 90%, or at least 95%. One embodiment relates to substantially pure Compound Va.

A further embodiment of the invention relates to the compound of formula (VI), preferably having an enantiomeric excess of at least 60%, at least 70%, at least 80%, at least 85%, at least 90%, at least 96%, preferably at least 98%,

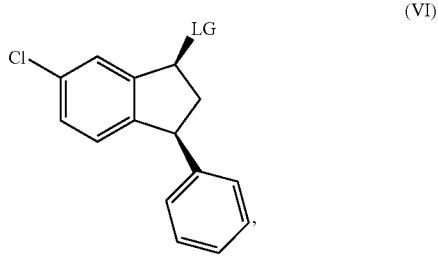

(VI)

wherein LG is a potential leaving group, preferably selected from the group consisting of a halogen, e.g. chloride, or a sulphonate. One embodiment relates to the diastereomeric purity of Compound VI; i.e. the compound having a diastereomeric excess of preferably at least 10% (10% diastereomeric excess means that the ratio of Compound VI to the trans diastereoisomer (e.g. (1S,3R)-3,5-dichloro-1-phenylindan when LG=Cl) is 55:45 in the mixture in question), at least 25% or at least 50%. One embodiment, relates to substantially pure Compound VI.

Accordingly, the invention also relates to a compound having the following formula (VIa),

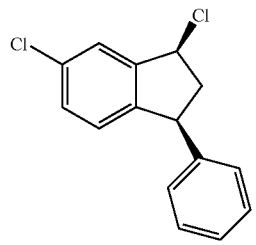

(VIa)

preferably having an enantiomeric excess of at least 60%, at least 70%, at least 80%, at least 85%, at least 90%, at least 96%, preferably at least 98%. One embodiment relates to the diastereomeric purity of the compound, i.e. the compound having a diastereomeric excess of, preferably at least 10% (10% diastereomeric excess means that the ratio of the compound to the trans diastereoisomer, (1S,3R)-3,5-dichloro-1-phenylindan, is 55:45 in the mixture in question), at least 25% or at least 50%. One embodiment relates to substantially pure Compound VI where LG is Cl.

As indicated above the invention in a particular interesting embodiment relates to:

Compound I or a salt thereof,
a pharmaceutical compositions as described herein comprising Compound I or a salt thereof,
a medical use as described herein for Compound I or a salt thereof,
wherein Compound I is having an enantiomeric excess of at least 60% (60% enantiomeric excess means that the ratio of Compound I to its enantiomer is 80:20 in the mixture in question), at least 70%, at least 80%, at least 85%, at least 90%, at least 96%, preferably at least 98%.

One embodiment relates to Compound I or a salt thereof and the uses as described herein, wherein Compound I is having a diastereomeric excess of at least 10% (10% diastereomeric excess means that the ratio of Compound I to the cis-(1S,3S) diastereoisomer is 55:45 in the mixture in question), at least 25%, at least 50%, at least 70%, at least 80%, at least 90%, at least 95%, at least 97%, preferably at least 98%.

One embodiment relates to substantially pure Compound I or a salt thereof; also for a medical use as described herein.

A further aspect relates to Compound I or a salt thereof, in particular the fumarate or maleate salt, obtainable, in particular obtained, by a method of the invention as described herein; also for a medical use as described herein.

The invention will be illustrated in the following non-limiting examples.

EXAMPLES

Pharmacology

Binding Assays

For all assays: Results are expressed as percent inhibition of control specific binding and the $IC_{50}$ values (concentration causing a half-maximal inhibition of control specific binding) are determined by non-linear regression analysis using Hill equation curve fitting. The inhibition constants ($K_i$) were calculated from the Cheng Prusoff equation $K_i=IC_{50}/(1+(L/K_D))$, where L equals the concentration of radioligand in the assay) and $K_D$ equals the affinity of the radioligand for the receptor.

Alpha-1 Adrenoceptors Subtyes

Chinese hamster ovary (CHO) cell lines expressing rat $alpha_{1d}$ and Baby hamster Kidney (BHK) cells expressing bovine $alpha_{1a}$ were generated using standard stable transfection techniques. The Rat-1 cell line expressing the hamster $alpha_{1b}$ receptor was obtained from University of Utah, Salt Lake City, Utah. Cell lines expressing the appropriate ($alpha_{1a}$, $alpha_{1b}$, $alpha_{1d}$) receptors were harvested and homogenized in ice-cold 50 mM Tris pH 7.7 using an Ultra-Turrax homogenizer and either stored at −80° C. on kept on ice until used. [$^3$H]Prazosin (0.3-0.5 nM) was used as radioligand assessing the affinity of subtypes of $alpha_1$ receptors. Total binding was determined using assay buffer and non-specific binding was defined in the presence of 1 µM WB-4101 for all subtypes of $alpha_1$ receptors. Aliquots were incubated 20 min at 25° C. In all assays bound and free radioactivity were separated by vacuum filtration on GF/B filters pretreated with Polyetyleneimine (PEI) and counted in a scintillation counter.

Alpha-1 Adrenoceptors (Inhibition of Binding of [$^3$H]Prazosine to Rat Alpha-1-Receptors)

By this method, the inhibition by drugs of the binding of [$^3$H]Prazosin (0.25 nM) to alpha-1 receptors in membranes from rat brain is determined in vitro. Method modified from Hyttel et al. *J. Neurochem.* 1985, 44, 1615-1622.

DA D1 Receptors:

Affinities towards human D1 receptors were determined at the contract laboratory Cerep using the catalog reference assay no 803-1h. Membranes from CHO cells expressing human recombinant D1 receptors were used. 0.3 nM [$^3$H]-SCH23390 was used as radioligand and compounds were tested in a serial dilution concurrently with the reference compound SCH23390 in order to assess the assay suitability. Aliqouts were incubates at 22° C. for 60 min and bound radioactivity are measured with a liquid scintillation counter.

Specific control binding to the D1 receptors was defined as the difference between the total binding determined without compound present and the non-specific binding determined in the presence of 1 µm SCH 23390.

DA D2 Receptors:

CHO cells expressing approximately 800 fmol/mg human recombinant D2 receptors were generated standard stable transfection techniques. Membranes were harvested using standard protocols and affinities were measured by the addition of a serial dilution of compound to a membrane preparation in a mixture of 50 mM Tris-HCl, 120 mM NaCl, 4 mM $MgCl_2$. 0.1 nM $^3$[H]-Spiperone was used as the radioligand assessing the affinity for the human D2 receptor. Total binding was determined in the presence of buffer and non-specific binding was determined in the presence of 10 µM haloperidol. The mixture was incubated for 30 minutes at 37° C., cooled briefly on ice. Bound and free radioactivity was separated by vacuum filtration on GF/C filters pretreated with 0.1% Polyetyleneime (PEI) and filters were counted in a scintillation counter.

Efficacy Assays

DA D1 Receptors:

The ability of the compounds to inhibit the D1 receptor mediated cAMP formation in a CHO cell line generated in-house stably expressing the human recombinant D1 receptor was measured as follows. Cells were seeded in 96-well plates at a concentration of 11000 cells/well 3 days prior to the experiment. On the day of the experiment the cells were washed once in preheated G buffer (1 mM $MgCl_2$, 0.9 mM $CaCl_2$, 1 mM IBMX in PBS) and the assay was initiated by addition of 100 µl of a mixture of 30 nM A68930 and test compound diluted in G buffer. The cells were incubated for 20 minutes at 37° C. and the reaction was stopped by the addition of 100 µl S buffer (0.1 M HCl and 0.1 mM $CaCl_2$) and the plates were placed at 4° C. for 1 hour. 68 µl N buffer (0.15 M NaOH and 60 mM NaAc) was added and the plates were shaken for 10 minutes. 60 µl of the reaction were transferred to cAMP FlashPlates (DuPont NEN) containing 40 µl 60 mM NaAc pH 6.2 and 100 µl IC mix (50 mM NaAc pH 6.2, 0.1% NaAzid, 12 mM $CaCl_2$, 1% BSA and 0.15 µCi/ml $^{125}$I-cAMP) were added. Following an 18-hour incubation at 4° C. the plates were washed once and counted in a Wallac TrLux counter.

DA D2 Receptors:

The ability of the compounds to inhibit the D2 receptor mediated inhibition of cAMP formation in CHO cells transfected with the human D2 receptor was measure as follows.

Cells were seeded in 96 well plates at a concentration of 8000 cells/well 3 days prior to the experiment. On the day of the experiment the cells were washed once in preheated G buffer (1 mM $MgCl_2$, 0.9 mM $CaCl_2$, 1 mM IBMX in PBS) and the assay was initiated by addition of 100 µl of a mixture of 1 µM quinpirole, 10 µM forskolin and test compound in G buffer. The cells were incubated 20 minutes at 37° C. and the reaction was stopped by the addition of 100 µl S buffer (0.1 M HCl and 0.1 mM $CaCl_2$) and the plates were placed at 4° C. for 1 hour. 68 µl N buffer (0.15 M NaOH and 60 mM NaAc) were added and the plates were shaken for 10 minutes. 60 µl of the reaction were transferred to cAMP FlashPlates (DuPont NEN) containing 40 µl 60 mM NaAc pH 6.2 and 100 µl IC mix (50 mM NaAc pH 6.2, 0.1% NaAzid, 12 mM $CaCl_2$, 1% BSA and 0.15 µCi/ml $^{125}$I-cAMP) were added. Following an 18-hour incubation at 4° C. the plates were washed once and counted in a Wallac TriLux counter.

Serotonin 5-HT2A Receptors 2 or 3 days before the experiment, CHO cells expressing 250 fmol/mg $S-HT_{2A}$ receptors are plated at a density sufficient to yield a mono-confluent layer on the day of the experiment. The cells are dye loaded ($Ca^{2+}$-kit from Molecular Devices and using Hank's balanced salt w/o phenol red, added 20 mM HEPES and pH adjusted to 7.4 with 2M NaOH as assaybuffer) for 60 minutes at 37° C. in a 5% $CO_2$ incubator at 95% humidity. Lacer intensity is set to a suitable level to obtain basal values of approximately 8000-10000 fluorescence units. The variation in basal fluorescence should be less than 10%. $EC_{50}$ values are assessed using increasing concentrations of test compound covering at least 3 decades. $IC_{50}$ values are assessed challenging the same range of concentrations of test substances with $EC_{85}$ of 5-HT. Test substances are added to the cells 5 minutes before the 5-HT. $K_i$ values were calculated using Cheng-Prusoff equation. % Stimulation of a concentration of the test compound is measured with respect to a maximal concentration of 5-HT (100%). % Inhibition of a concentration of the test compound is measured as the percentage with which the response of $EC_{85}$ of 5-HT is lowered. Maximum inhibition is the level of inhibition the curve reaches. It is expressed as the percentage inhibition at that level and used to distinguish full and partial antagonists.

In Vitro Determination of the Interaction of Compounds with CYP2D6 (CYP2D6 Inhibitor Assay Principle: The inhibition of human CYP2D6 is assessed using microsomes prepared from baculovirus/insect cells cDNA expressing CYP2D6 as enzyme sources and the specific CYP2D6 substrate AMMC (3-[2-(N,N-diethyl-N-methylammonium)-ethyl]-7-methoxy-4-methylcoumarin). AMMC is O-demethylated to AHMC (3-[2-(N,N-diethylamino)ethyl]-7-hydroxy-4-methylcoumarin) which is detected by measuring appearance of fluorescence. Preferred compounds of the present invention exhibit an IC50 higher than 5 micromolar for CYP2D6 activity, the IC50 being the concentration of the compound that gives 50% of inhibition of the CYP2D6 activity.

Material and Methods:

Microsomes prepared from baculovirus/insect cells cDNA expressing CYP2D6 were obtained from BD Biosciences (Gentest 456217). Fluorescence measured Ex. (405 nm) Em. (465 nm) by a SpectroFluor Plus Plate Reader (Tecan Nordic). Incubations with the recombinant CYP2D6 micrsomes contained 1.5 pmol of the recombinant CYP2D6 in 0.2 ml total volume 100 mM phosphate buffer at pH 7.4 containing 1.5 AMMC (3-[2-(N,N-diethyl-N-methylammonium)-ethyl]-7-methoxy-4-methylcoumarin) with a low NADPH-regenerating system consisting of 0.0082 mM NADP$^+$, 0.41 mM glucose 6-phosphate, 0.41 mM magnesium chloride and 0.4 units/ml glucose-6-phoshate dehydrogenase. The incubation time was 45 min and the incubations were quenched by addition of 0.075 ml 80% Acetonitrile 20% 0.5 M Tris base. All chemicals were of analytical grade from Sigma (St. Louis, Mo.). IC50 curves were produced using 8 concentration between 40 and 0.02 micromolar of the compounds to be tested dissolved in DMSO (dimethyl sulfoxide)—final conc. in incubations were below 1.0% (Modified from N. Chauret et. al. DMD Vol. 29, Issue 9, 1196-1200, 2001). The $IC_{50}$ values were calculated by linear interpolation.

QT-Interval

Anaesthetised Rabbit:

The model described in the following was originally designed as a proarrhytmic model by Carlsson et al, [J Cardiovasc Pharmacol. 1990;16:276-85.] and has been modified to fit into screening set-up as described below under "animal preparation".

Animal Preparation

Male rabbits (HsdIf:NZW, outbreed) weighing 2.0-2.8 kg were purchased from Harlan (The Netherlands). Individual body weights were measured and recorded on the day of experiment. General anaesthesia was induced via the marginal ear vein by an intravenous infusion of pentobarbital (10 mg/ml, 18 mg/kg) followed by (alpha-chloralose (100 mg/kg, infusion volume 4 ml/kg administered over a 20 min period). The trachea was cannulated and the rabbits were ventilated with air at 45 strokes per min and a tidal volume of 6 ml/kg. A vascular catheter was implanted in the jugular vein for test compound administration. Additional catheters were implanted in the left carotid artery for blood sampling and blood pressure monitoring. Needle electrodes were placed subcutaneously to record the standard bipolar lead II: the negative electrode was placed in front of the right shoulder, the positive electrode close to the left loin.

Experimental Protocol

Following a short period of equilibration, pre-dose values were obtained at −20, −10 and 0 min prior to an IV bolus administration of vehicle or test compound. The effect of the bolus administration was followed for a 40 min period.

Data Sampling and Calculating

ECG, blood pressure and HR were continuously recorded on a Maclab 8/s using the Chart software v3.6.1 for the Macintosh computer. The sampling frequency was 1000 Hz. Effects on the electrocardiogram (PQ-, QRS-, QT-, QTc-intervals and heart rate) and mean arterial blood pressure (MAP) were recorded and measured electronically.

Analytical Methods

The enantiomeric excess of compound (Va) in Example 1a is determined by chiral HPLC using a CHIRALCEL® OD column, 0.46 cm ID×25 cm L, 10 µm at 40° C. n-Hexan/ethanol 95:5 (vol/vol) is used as mobile phase at a flow rate of 1.0 ml/min, detection is performed using a UV detector at 220 nm.

HPLC Analysis for Conversion Rate Used for Examples 1b:

Column: A Lichrospher RP-8 column, 250×4 mm (5 µm particle size)

Eluent: Buffered MeOH/water prepared as follows: 1.1 ml Et$_3$N added to 150 ml water, 10% H$_3$PO$_4$(aq) is added to pH=7 and water is added to a total of 200 ml. The mixture is added to 1.8 L MeOH.

The enantiomeric excess of compound (Va) in example 1b is determined by chiral HPLC using a CHIRALPAK® AD column, 0.46 cm D×25 cm L, 10 µm at 21° C. Heptane/ethanol/Diethylamine 89.9:10:0.1 (vol/vol/vol) is used as mobile phase at a flow rate of 1.0 ml/min, detection is performed using a UV detector at 220 nm.

The enantiomeric excess of compound (I) is determined by fused silica capillary electrophoresis (CE) using the following conditions: Capillar: 50 µm ID×48.5 cm L, run buffer: 1.25 mM β cyclo dextrin in 25 mM sodium dihydrogen phosphate, pH 1.5, voltage: 16 kV, temperature: 22° C., injection: 40 mbar for 4 seconds, detection: column diode array detection 195 nm, sample concentration: 500 µg/ml. In this system, Compound I has a retention time of approximately 10 min, and the other enantiomer has a retention time of approximately 11 min.

$^1$H NMR spectra is recorded at 500.13 MHz on a Bruker Avance DRX500 instrument or at 250.13 MHz on a Bruker AC 250 instrument. Chloroform (99.8% D) or dimethyl sulfoxide (99.8% D) is used as solvents, and tetramethylsilane (TMS) is used as internal reference standard.

The cis/trans ratio of compound I is determined using $^1$H NMR as described in Bøgesø et al., J. Med. Chem. 1995, 38,4380-4392 (page 4388, right column). The cis/trans ratio of compound VI is determined by $^1$H NMR in chloroform, using the integrals of the signal at 5.3 ppm for the cis isomer and the signal at 5.5 ppm for the trans isomer. Generally, a content of approximately 1% of the undesired isomer can be detected by NMR.

The Melting Points are measured using Differential Scanning Calorimetry (DSC). The equipment is a TA-Instruments DSC-2920 calibrated at 5°/min to give the melting point as onset value. About 2 mg of sample is heated 5°/min in a loosely closed pan under nitrogen flow.

Synthesis

Synthesis of Key Starting Material

Compound V was synthesised from IV by reduction with sodium borohydride (NaBH$_4$) adapting a method described in Bøgesø J. Med. Chem. 1983, 26, 935, using ethanol as solvent, and performing the reaction at approximately 0° C. Both compounds are described in Bøgesø et al. J. Med. Chem.

1995, 38, 4380-4392. Compound IV was synthesised from II using the general procedures described in Sommer et al., *J. Org. Chem.* 1990, 55, 4822, which also describes II and the synthesis thereof.

EXAMPLE 1a

Synthesis of (1S,3S)-6-chloro-3-phenylindan-1-ol (Va) by use of Chiral Chromatography Racemic cis-6-chloro-3-phenylindan-1-ol (V) (492 grams) is resolved by preparative chromatography, using a CHIRAL-PAK® AD column, 10 cm ID×50 cm L, 10 µm at 40° C. Methanol is used as mobile phase at a flow rate of 190 ml/min, detection is performed using a UV detector at 287 nm. The racemic alcohol (V) is injected as a 50,000 ppm solution in methanol; 90 ml is injected with intervals of 28 min. All the fractions, which contain the title compound with more than 98% enantiomeric excess, are combined and evaporated to dryness using a rotary evaporator, followed by drying "in vacuo" at 40° C. Yield 220 grams as a solid. Elemental analysis and NMR conform to the structure, the enantiomeric excess is higher than 98% according to chiral HPLC, $[\alpha]_D^{20}$+ 44.5° (c=1.0, methanol).

EXAMPLE 1b

Synthesis of (1S,3S)-6-chloro-3-phenylindan-1-ol (Va) by use of Enzymatic Resolution

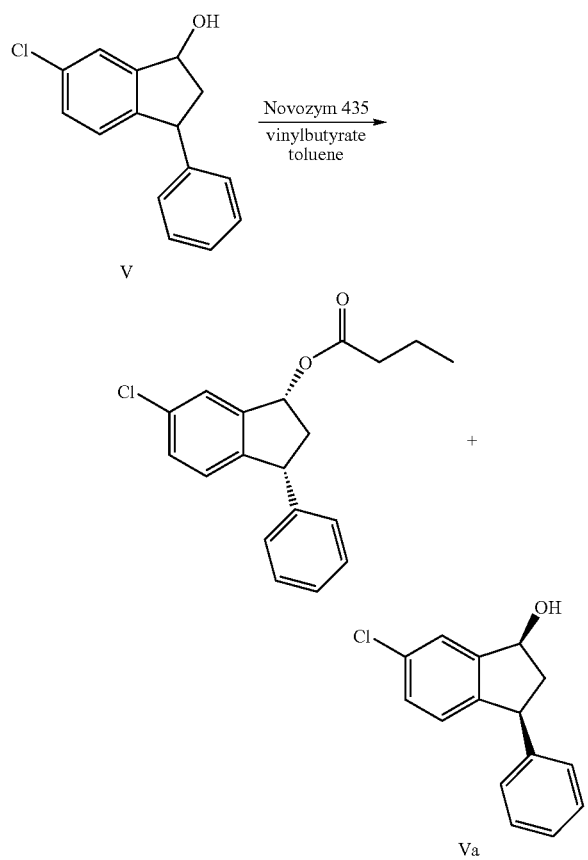

Compound V (5 g, 20.4 mmol) is dissolved in 150 ml anhydrous toluene. 0.5 g Novozym 435 (Candida Antarctica lipase B) (Novozymes A/S, Fluka Cat.-No. 73940) is added followed by vinylbutyrate (13 ml, 102.2 mmol). The mixture is stirred using mechanical stirrer at 21° C. After 1 day, an additional 0.5 g Novozym 435 is added. After 4 days at a conversion of 54%, the mixture is filtered and concentrated in vacuo to obtain an oil containing a mixture of (1R, 3R)-cis-6-chloro-3-phenylindan-1-ol-butyrate ester and desired compound Va with an enantiomeric excess of 99.2% (99.6% compound Va and 0.4% (1R, 3R)-cis-6-chloro-3-phenylindan-1-ol).

EXAMPLE 2

Synthesis of (1S,3S)-3,5-dichloro-1-phenylindan (VI, LG=Cl)

Cis-(1S,3S)-6-chloro-3-phenylindan-1-ol (Va) (204 grams) obtained as described in Example 1a is dissolved in THF (1500 ml) and cooled to −5° C. Thionyl chloride (119 grams) is added dropwise as a solution in THF (500 ml) over a period of 1 h. The mixture is stirred at room temperature over night. Ice (100 g) is added to the reaction mixture. When the ice has melted the water phase (A) and the organic phase (B) are separated, and the organic phase B is washed twice with saturated sodium bicarbonate (200 ml). The sodium bicarbonate phases are combined with water phase A, adjusted to pH 9 with sodium hydroxide (28%), and used to wash the organic phase B once again. The resulting water phase (C) and the organic phase B are separated, and the water phase C is extracted with ethyl acetate. The ethyl acetate phase is combined with the organic phase B, dried with magnesium sulphate, and evaporated to dryness using a rotary evaporator, giving the title compound as an oil. Yield 240 grams, which is used directly in the example 5. Cis/trans ratio 77:23 according to NMR.

EXAMPLE 3

Synthesis of 3,3-dimethylpiperazin-2-one

Potassium carbonate (390 grams) and ethylene diamine (1001 grams) are stirred with toluene (1.50 l). A solution of ethyl 2-bromoisobutyrate (500 grams) in toluene (750 ml) is added. The suspension is heated to reflux over night, and filtered. The filter cake is washed with toluene (500 ml). The combined filtrates (volume 4.0 l) are heated on a water bath and distilled at 0.3 atm. using a Claisen apparatus; first 1200 ml distillate is collected at 35° C. (the temperature in the mixture is 75° C.). More toluene is added (600 ml), and another 1200 ml distillate is collected at 76° C. (the temperature in the mixture is 80° C.). Toluene (750 ml) is added again, and 1100 ml of distillate is collected at 66° C. (temperature in the mixture 71° C.). The mixture is stirred on an ice bath and inoculated, whereby the product precipitates. The product is isolated by filtration, washed with toluene, and dried over night in a vacuum oven at 50° C. Yield 171 g (52%) of 3,3-dimethylpiperazin-2-one. NMR consistent with structure.

EXAMPLE 4

Synthesis of 2,2-dimethylpiperazine

A mixture of 3,3-dimethylpiperazin-2-one (8.28 kg, 64.6 mol) and tetrahydrofuran (THF) (60 kg) is heated to 50-60° C. giving a slightly unclear solution. THF (50 kg) is stirred under nitrogen, and LiAlH$_4$ (250 g, in a soluble plastic bag, from Chemetall) is added, which gives a slow evolution of gas. After gas evolution has ceased, more LiAlH$_4$ is added (a total of 3.0 kg, 79.1 mol, is used), and the temperature rises from 22° C. to 50° C. because of an exoterm. The solution of 3,3-dimethylpiperazin-2-one is added slowly over 2 hours at 41-59° C. The suspension is stirred for another hour at 59° C. (jacket temperature 60° C.). The mixture is cooled, and water (3 l) is added over two hours, keeping the temperature below 25° C. (it is necessary to cool with a jacket temperature of 0° C.). Then sodium hydroxide (15%, 3.50 kg) is added over 20 minutes at 23° C., cooling necessary. More water (9 l) is added over half an hour (cooling necessary), and the mixture is stirred over night under nitrogen. Filter agent Celit (4 kg) is added, and the mixture is filtered. The filter cake is washed with THF (40 kg). The combined filtrates are concentrated in the reactor until the temperature in the reactor is 70° C. (distillation temperature 66° C.) at 800 mbar. The remanence (12.8 kg) is further concentrated on a rotavapor to approximately 10 l. Finally, the mixture is fractionally distilled at atmospheric pressure, and the product is collected at 163-4° C. Yield 5.3 kg (72%). NMR complies with the structure.

EXAMPLE 5

Synthesis of trans-1-((1R,3S)-6-chloro-3-phenylindan-1-yl)-3,3-dimethylpiperazinium (Compound I) Hydrogen Maleate Salt Cis-(1S,3S)-3,5-dichloro-1-phenylindan (VI, LG=Cl) (240 g) is dissolved in butan-2-one (1800 ml). Potassium carbonate (272 g) and 2,2-dimethyl piperazine (prepared in Example 4) (113 g) are added and the mixture is heated at reflux temperature for 40 h. To the reaction mixture is added diethyl ether (2 l) and hydrochloric acid (1M, 6 l). The phases are separated, and pH in the water phase is lowered from 8 to 1 with concentrated hydrochloric acid. The water phase is used to wash the organic phase once again in order to ensure, that all product is in the water phase. Sodium hydroxide (28%) is added to the water phase until pH is 10, and the water phase is extracted twice with diethyl ether (2 l). The diethyl ether extracts are combined, dried with sodium sulphate, and evaporated to dryness using a rotary evaporator. Yield 251 grams of the title compound as an oil. Cis/trans ratio, 82:18 according to NMR. The crude oil (ca. 20 grams) was further purified by flash chromatography on silicagel (eluent: ethyl acetate/ethanol/triethylamine 90:5:5) followed by evaporation to dryness on a rotary evaporator. Yield 12 grams of the title compound as an oil (cis/trans ratio, 90:10 according to NM). The oil is dissolved in ethanol (100 ml), and to this solution is added a solution of maleic acid in ethanol to pH 3. The resulting mixture is stirred at room temperature for 16 hours, and the formed precipitate is collected by filtration. The volume of ethanol is reduced and another batch of precipitate is collected. Yield 3.5 gram solid (no cis isomer is detected according to NMR) of the title compound. Enantiomeric excess is >99%. Melting point 175-178° C. NMR complies with the structure.

EXAMPLE 6

Synthesis of Compound I

A mixture of trans-1-((1R,3S)-6-chloro-3-phenylindan-1-yl)-3,3-dimethylpiperazinium hydrogen maleate (I) (9.9 grams), concentrated aqueous ammonia (100 ml), brine (150 ml) and ethyl acetate (250 ml) is stirred at room temperature for 30 min. The phases are separated, and the aqueous phase is extracted with ethyl acetate once more. The combined organic phases are washed with brine, dried over magnesium sulphate, filtered and evaporated to dryness in vacuo. Yield 7.5 grams of oil. NMR complies with the structure.

EXAMPLE 7

Synthesis of trans-1-((1R,3S)-6-chloro-3-phenylindan-1-yl)-3,3-dimethylpiperazinium (Compound I) Fumarate Salt A solution of trans-1-((1R,3S)-6-chloro-3-phenylindan-1-yl)-3,3-dimethylpiperazine (obtained as described in example 6) (1 g) is dissolved in acetone (100 mL). To this solution is added a solution of fumaric acid in ethanol until pH of the resulting solution is 4. The resulting mixture is cooled in an ice bath for 1.5 hours whereby a precipitate is formed. The solid compound is collected by filtration. The compound was dried in vacuo giving a white solid compound (1.0 g). Enantiomeric excess is >99%. Melting point 193-196° C. NMR complies with the structure.

The invention claimed is:

1. A compound having the name of trans-1-((1R,3S)-6-chloro-3-phenylindan-1-yl)-3,3-dimethylpiperazine and a formula of:

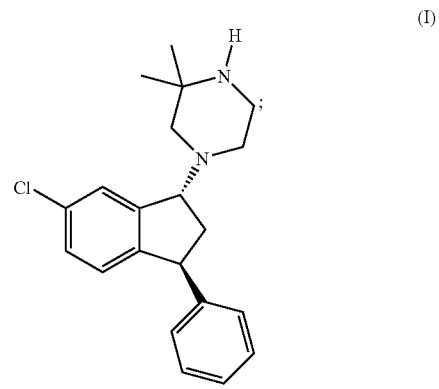

(I)

or a pharmaceutically acceptable salt thereof; wherein the compound is stereochemically pure.

2. A pharmaceutical composition comprising the compound of claim 1 and at least one pharmaceutically acceptable carrier, filler or diluent.

3. The pharmaceutical composition of claim 2, wherein the compound is present in an enantiomeric excess of at least 90%.

4. A method of treating a subject suffering from a disease or disorder comprising administering to the subject a therapeutically effective amount of the compound of claim 1, wherein the disease or disorder is selected from the group consisting of schizophrenia, an anxiety disorder, a depression, Schizophreniform Disorder, Schizoaffective Disorder, Delusional Disorder, Brief Psychotic Disorder, Shared Psychotic Disorder and mania in bipolar disorder.

5. The method of claim 4, wherein the disease or disorder is schizophrenia, Schizophreniform Disorder, Schizoaffective Disorder, Delusional Disorder, Brief Psychotic Disorder, Shared Psychotic Disorder or mania in bipolar disorder.

6. The method of claim 5, wherein the schizophrenia comprises positive symptoms.

7. The method of claim 5, wherein the schizophrenia comprises negative symptoms.

8. The method of claim 5, wherein the schizophrenia comprises depressive symptoms.

9. The method of claim 4, wherein the subject is treated with at least one other medicament.

10. A method of treating a subject suffering from a disease or disorder comprising administering to the subject a therapeutically effective amount of the compound of claim 1, wherein: the disease or disorder is selected from the group consisting of schizophrenia, an anxiety disorder, a depression, Schizophreniform Disorder, Schizoaffective Disorder, Delusional Disorder, Brief Psychotic Disorder, Shared Psychotic Disorder and mania in bipolar disorder; and the compound is present in an enantiomeric excess of at least 90%.

* * * * *

UNITED STATES PATENT AND TRADEMARK OFFICE
CERTIFICATE OF CORRECTION

PATENT NO. : 7,772,240 B2
APPLICATION NO. : 10/568292
DATED : August 10, 2010
INVENTOR(S) : Bang-Andersen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 190 days.

Signed and Sealed this
Twenty-second Day of March, 2011

David J. Kappos
*Director of the United States Patent and Trademark Office*